United States Patent
Teng et al.

[11] Patent Number: 6,154,285
[45] Date of Patent: Nov. 28, 2000

[54] SURFACE TREATMENT FOR OPTICAL IMAGE CAPTURING SYSTEM

[75] Inventors: Harry H. Teng, Stanford, Calif.; Sung-Chan Jo, Seoul, Rep. of Korea

[73] Assignee: SecuGen Corporation, San Jose, Calif.

[21] Appl. No.: 09/217,558

[22] Filed: Dec. 21, 1998

[51] Int. Cl.[7] .............................. G01N 21/55; G06K 9/74
[52] U.S. Cl. ............................................. 356/445; 356/71
[58] Field of Search ........................... 356/445, 71, 376; 382/108, 116, 124

[56] References Cited

U.S. PATENT DOCUMENTS

| | | | |
|---|---|---|---|
| 3,975,711 | 8/1976 | McMahon | 340/146.3 |
| 4,120,585 | 10/1978 | DePalma et al. | 356/71 |
| 4,681,435 | 7/1987 | Kubota et al. | 356/71 |
| 4,832,485 | 5/1989 | Bowles | 356/71 |
| 4,983,415 | 1/1991 | Arndt et al. | 427/1 |
| 5,051,576 | 9/1991 | Schiller | 250/227.11 |
| 5,096,290 | 3/1992 | Ohta | 356/71 |
| 5,177,435 | 1/1993 | Kiyokawa | 324/158 |
| 5,210,588 | 5/1993 | Lee | 356/71 |
| 5,222,153 | 6/1993 | Heiswenger | 382/4 |
| 5,233,404 | 8/1993 | Lougheed et al. | 356/71 |
| 5,732,148 | 3/1998 | Keagy et al. | 382/124 |
| 5,737,071 | 4/1998 | Arndt | 356/71 |

FOREIGN PATENT DOCUMENTS

| | | |
|---|---|---|
| 0 867 828 A2 | 9/1998 | European Pat. Off. . |
| 0 867 829 | 9/1998 | European Pat. Off. . |

*Primary Examiner*—Frank G. Font
*Assistant Examiner*—Michael P. Stafira
*Attorney, Agent, or Firm*—Morrison & Foerster LLP

[57] ABSTRACT

Disclosed is an image capturing system including a light refractor, a light source, and a light receptor. The light refractor can be a triangular prism and includes an imaging surface against which a fingerprint or other object to be imaged is placed. The imaging surface includes at least a first layer of material which has a first part which includes a polymer and a second part which includes a fluid retained within the polymer. The fluid of the first layer can fill irregularities in the ridges of a fingerprint placed on the imaging surface. This allows a higher contrast, sharper fingerprint image to be captured. The imaging surface can also includes a second layer of protective material interposed between the first layer of material and the surface of the prism to reduce breakdown or deterioration of the first layer of material due to adhesives used on the surface of the prism.

16 Claims, 8 Drawing Sheets

SURFACE TREATMENT FOR OPTICAL IMAGE CAPTURING SYSTEM

BACKGROUND

1. Technical Field

The present invention is directed to a system for capturing images of patterned objects. In particular, the present invention includes a treatment for an imaging surface of a fingerprint image capturing system to provide high contrast images of the fingerprint.

2. Related Art

Patterned object recognition systems are becoming common in industrial and commercial settings and have a variety of uses. Recently, manufacturers have been attempting to reduce costs associated with pattern recognition systems to make them more viable for consumer use. One such consumer application for pattern recognition systems includes fingerprint image acquisition and recognition. Such a system is useful, for example, to enhance computer security by reading a potential user's fingerprint to compare with the fingerprints of users authorized to use a computer or access certain files or functions of a computer. Such a system could, for example, take the place of a security system that uses a login name and password.

The first thing such a fingerprint recognition system, or any pattern recognition system, must be able to do is to accurately acquire the fingerprint, or other pattern, for analysis. A number of mechanisms exist for such acquisition of pattern data. For example, U.S. Pat. Nos. 3,975,711; 4,681,435; 5,051,576; 5,177,435 and 5,233,404 all disclose apparatuses for acquiring an image of a patterned object.

Figure 1:
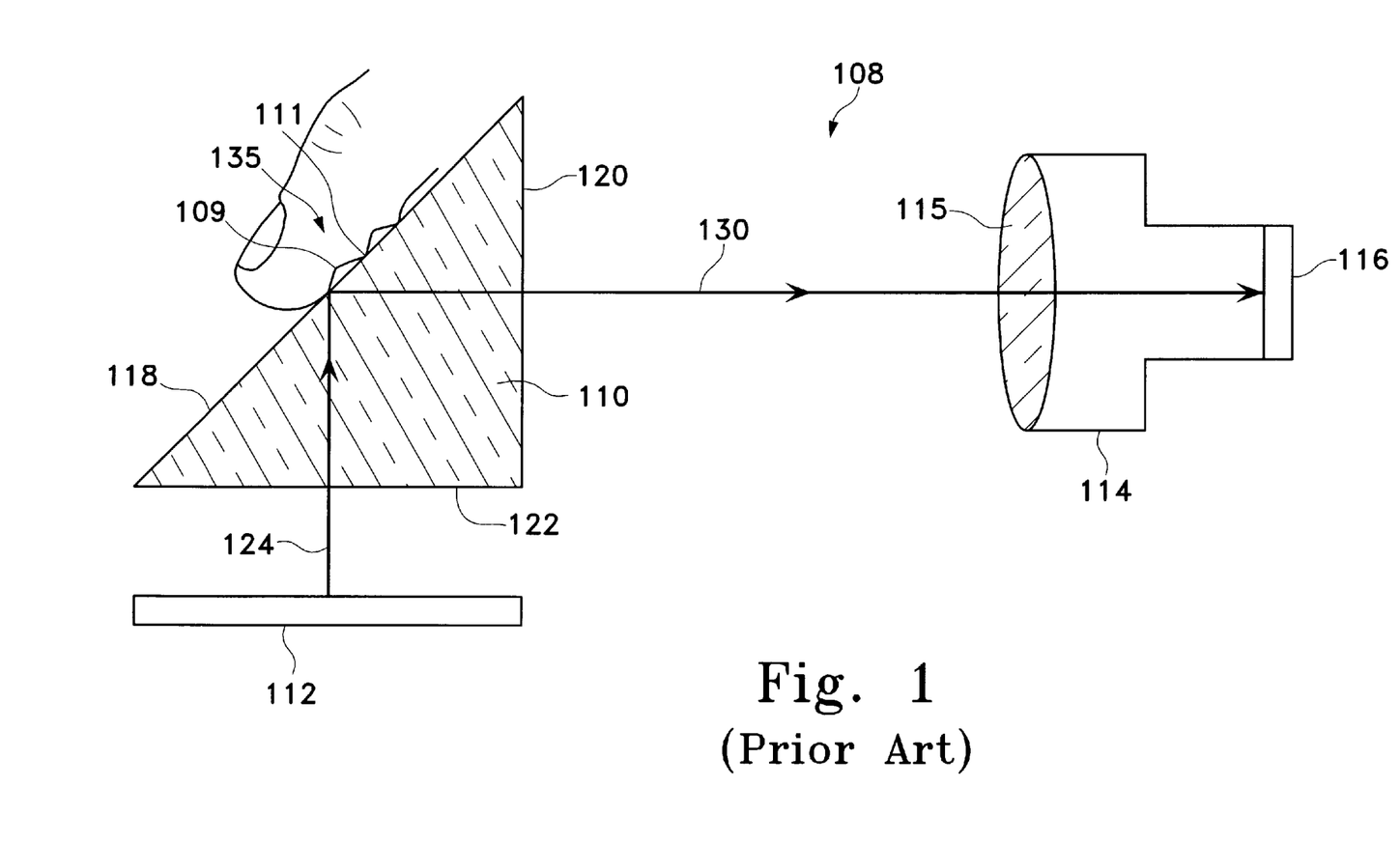
FIG. 1 is a schematic side view of a prior art image capturing system including an optical prism, a light source, and a light receptor.

FIG. 1 shows a schematic diagram of one such prior art optical fingerprint capturing and recognition system. In FIG. 1, an image capturing system 108 includes a light source 112, an optical prism 110, and a light detector 114. The prism 110 includes an imaging surface 118, a light receiving surface 122, and a viewing surface 120. Imaging surface 118 is the surface against which a patterned object, such as a fingerprint, is placed for imaging. The light source 112, which may, for example, include one or more light emitting diodes (LEDs), is placed adjacent to light receiving surface 122 and generates incident light 124 that is transmitted to the optical prism 110.

Generally, incident light 124 strikes imaging surface 118 and can either pass through, reflect from, or scatter off of imaging surface 118 to form an image of fingerprint 135. Reflected and/or scattered light 130 passes out of viewing surface 120 of prism 110 and through light detector 114 located adjacent to viewing surface 120. Light detector 114 may contain one or more optical lenses 115 and an image sensor 116 for capturing optical light images and converting them into electrical signals. Such an image sensor 116 could include, for example, a charge coupled device (CCD) or complementary metal oxide semiconductor (CMOS) chip. The electrical signals can be processed by processing electronics and/or software (not shown) and stored in a form to allow comparison with other fingerprint images.

As shown in FIG. 1, fingerprint 135 has both valleys 109 and ridges 111. There are at least two methods by which an image capturing system such as system 108 can image valleys 109 and ridges 111 of fingerprint 135. Both methods rely on a fingerprint ridge 111 being in contact with imaging surface 118 and a fingerprint valley 109 being above and out of contact with imaging surface 118. In a first method, known as an "absorption" method, incident light 124 which strikes a region of imaging surface 118 where a fingerprint ridge 111 is in contact therewith is substantially absorbed or scattered by ridge 111. Incident light 124 which strikes a region of imaging surface 118 where there is a fingerprint valley 109, however, is totally internally reflected from imaging surface 118 to enter light detector 114. A portion of the absorbed and/or scattered light from fingerprint ridges 111, however, is not picked up by light detector 114. Accordingly, in an absorption system, the image of fingerprint 135 is relatively bright at fingerprint valleys 109 and relatively dark at fingerprint ridges 111.

In a second method, known as a scattering method, incident light 124 is projected onto imaging surface 118 such that in regions of a fingerprint ridge 111, incident light 124 is scattered into prism 110 and in regions of a fingerprint valley 109, incident light 124 substantially passes through imaging surface 118. Light detector 114 picks up the scattered light and does not pick up the light which passes through imaging surface 118. Thus, in a scattering system, the image of a fingerprint 135 is relatively dark at fingerprint valleys 109 and relatively bright at fingerprint ridges 111.

In either a scattering system or an absorption system, the ability of an image capture system to create a high contrast, accurate fingerprint image is dependent upon the fingerprint ridges 111 touching the imaging surface 118 and fingerprint valleys 109 not touching imaging surface 118. Specifically, in an absorption system, it is the contact between the fingerprint ridge 111 and imaging surface 118 which causes the absorption and/or scattering of incident light 124 and the lack of contact between a fingerprint valley 109 and the imaging surface 118 which allow total internal reflection of incident light 124 to create an image of the fingerprint 135. In a scattering system, it is the contact between a fingerprint ridge 111 and imaging surface 118 which causes incident light 124 to be scattered into lens assembly 114 and the lack of contact between a fingerprint valley 109 and imaging surface 118 which allows incident light 124 to pass through imaging surface 118.

Accordingly, to generate an accurate image of a fingerprint 135, fingerprint ridges 111 should have relatively complete contact with imaging surface 118.

Figure 2:
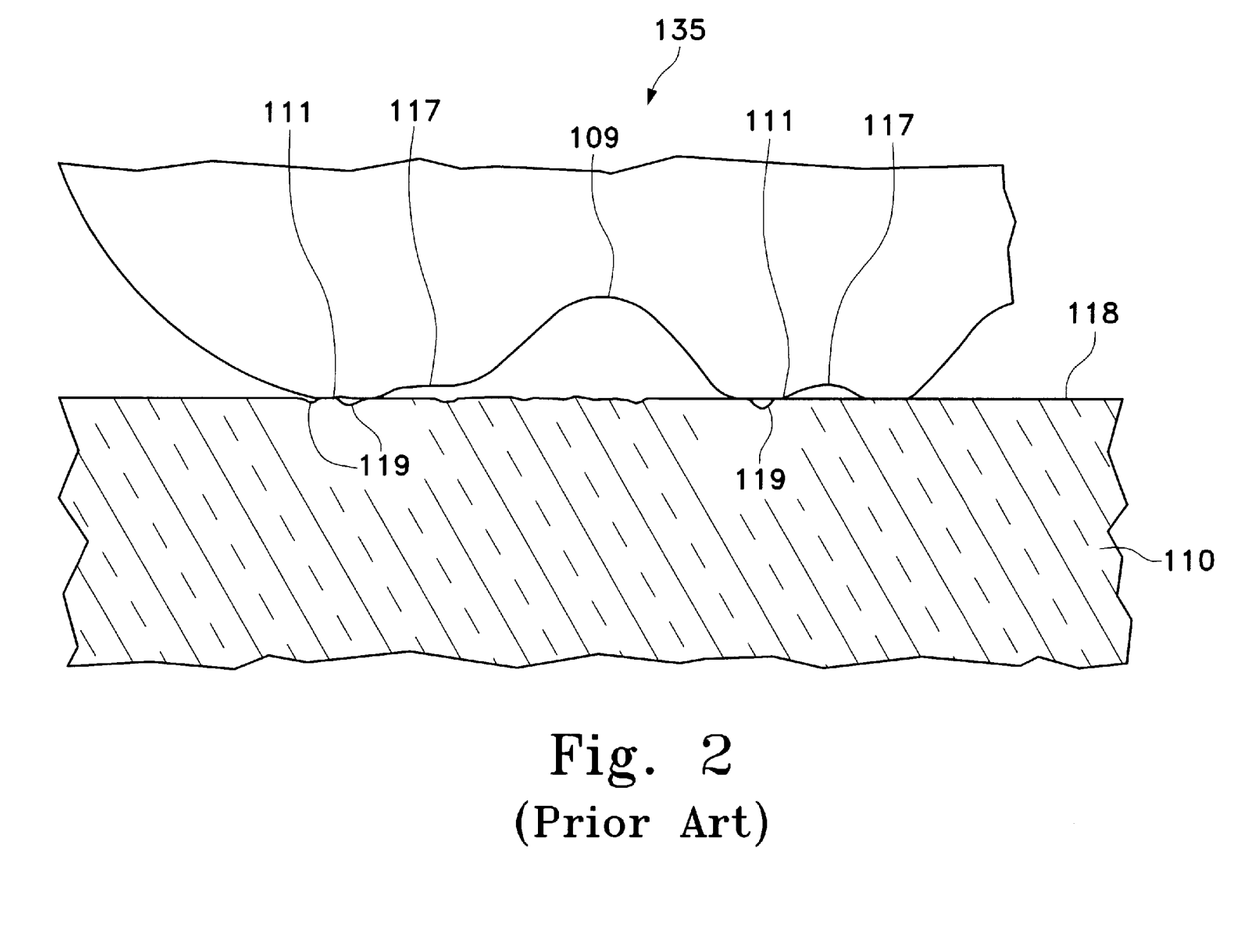
FIG. 2 is a partial side view of the optical prism shown in FIG. 1 with a fingerprint placed on an imaging surface thereof.

However, at least two difficulties can arise in connection with establishing relatively complete contact between fingerprint ridges and imaging surface 118. First, if prism 110 is formed from glass, imaging surface 118 will have been ground by an abrasive substance to smooth imaging surface 118. While this grinding process leaves imaging surface 118 relatively smooth on a macroscopic scale, as shown in FIG. 2, which is an enlarged side schematic view of imaging surface 118, the abrasive substance used to grind imaging surface 118 can form indentations or pits 119 in imaging surface 118. A fingerprint ridge 111 will generally not fill in a pit 119 when fingerprint 135 is placed against imaging surface 118. Accordingly, pits 119 cause an area of non-contact between imaging surface 118 and fingerprint ridge 111. For the reasons explained above, this can cause deterioration of a fingerprint image generated by image capturing system 108.

A second difficulty in establishing relatively complete contact between a fingerprint ridge 111 and imaging surface 118 is also illustrated in FIG. 2. As shown, the ridges 111 of fingerprint 135 are generally uneven and have gaps or irregularities 117. Therefore, fingerprint ridges 111 may not make complete contact with imaging surface 118. And, the irregularities 117 of fingerprint ridges 111 which are not actually touching imaging surface 118 will not, or will only partially, scatter or absorb incident light 124. This can cause a blurry or un-clear fingerprint image and/or can reduce the contrast of a fingerprint image.

Prior art fingerprint readers have addressed these problems in various ways. For example, U.S. Pat. No. 5,737,071 issued to Arndt on Apr. 7 1998 ("Arndt") is directed to a method for enhancing live-scan fingerprint reader images. Arndt discloses providing an absorbent pad containing chemicals to coat the surface of a person's finger whose fingerprint is to be taken. After being coated with chemicals from the pad, the person's finger is placed against a window or platen of the fingerprint reader to allow an image to be taken. The chemicals from the pad tend to fill in the regions of the fingerprint ridge/platen interface where the fingerprint ridge does not quite touch the platen. The chemical which fills in these regions can act as a fingerprint ridge which is fully touching the platen to scatter and/or absorb the incident light. However, not enough chemical is retained on the fingerprint to fill in the fingerprint valleys. Thus, incident light will still totally internally reflect from (absorption system) or pass through (scattering system) the platen at fingerprint valleys. In this way, a higher contrast, sharper fingerprint image can be obtained.

However, there are some difficulties with the method and apparatus disclosed in Arndt. First, the user of the fingerprint reader must use a separate absorbent pad prior to using the scanner. This can make use of such a system inconvenient for use as a PC security system. Additionally, chemical residue can be left on the platen after a fingerprint image is captured. This chemical residue can interfere with subsequent capturing of fingerprint images and collect debris which can further interfere with capturing of fingerprint images. Further, if substantial enough, such chemical residue can make it appear as though a fingerprint is still on the window. Thus, the fingerprint ready may be able to be "tricked" into reading a false match of a fingerprint, though there is no actual fingerprint on the window.

A second example of a prior art system which has attempted to overcome some of the difficulties of fingerprint image capture is disclosed in U.S. Pat. No. 5,096,290 issued to Ohta on Mar. 17, 1992 ("Ohta"). Ohta discloses a fingerprint imaging apparatus which includes a prism having a window against which a fingerprint to be imaged is placed. A layer of transparent material is placed over the window. The layer of material can be natural or synthetic rubbers including silicon and epoxy. When a fingerprint is placed against the material layer, the material tends to deform to accommodate slightly recessed areas of fingerprint ridges placed against the material layer. Thus, the material can act to improve the contrast and sharpness of a fingerprint image.

However, the adhesive with which the material layer is adhered to the surface of the window can contain solvents which can be vaporized around the surface of the layer. And, it has been found that some transparent materials including natural and synthetic rubbers as disclosed by Ohta, can break down and become brittle and or clouded as a result of exposure to these vapors. It has also been found that placing a fingerprint against the pliant material layer can accelerate this breakdown process. As such, the pliant material layer disclosed by Ohta could become brittle with use and, as such, would no longer enhance fingerprint image contrast and sharpness. Additionally, fingerprints can contain oily substances which can leave a residue on the surface of the window which is used to image the fingerprint. Such oily residue can interfere with subsequent capturing of fingerprint images and collect debris which can further interfere with capturing of fingerprint images. Further, as noted above, oily fingerprint substances can leave an image of a fingerprint on the window which can "trick" the fingerprint reader into registering a false match.

As the above discussion makes clear, there is room for improvement in fingerprint imaging devices. Specifically, a fingerprint imaging system should be able to quickly and reliably capture a high contrast, sharp image. The system should also be relatively easy to use and manufacture.

SUMMARY OF THE INVENTION

The present invention is directed to an apparatus for imaging a patterned object such as a fingerprint. An image surface treatment is disclosed which provides for quick, reliable image capture to produce a high contrast, sharp image of a patterned object such as a fingerprint. The apparatus includes a transparent light refractor, such as a triangular prism, for reflecting and refracting light which has an imaging surface against which a patterned object to be imaged is placed. The apparatus also includes a light detector and a light source, both adjacent to the light refractor. The light detector is for detecting an image of the patterned object and the light source directs light towards the imaging surface to generate an image of the patterned object. A first layer of transparent material is provided as part of the imaging surface. The first layer of material has two parts; a first part is a polymer and a second part is a fluid which is retained by the polymer. When a patterned object to be imaged is placed against the first layer, the fluid can fill irregularities and gaps in the patterned object. Additionally, the fluid in the first layer of material can dissolve fingerprint oil residue which might otherwise remain on the imaging surface and cause interference with the capturing of subsequent images.

The present invention can also include a second layer of transparent material interposed between the first layer of material and the first surface of the light refractor. The second layer of material acts to protect the first layer of material from adhesives which might be used on the first surface of the prism.

By providing the first layer of material, it is possible to obtain more complete contact between a fingerprint and the imaging surface of the light refractor. Thus, the apparatus of the present invention can advantageously produce a high contrast, sharp images of a patterned object, such as a fingerprint. Additionally, by providing a second layer, the first layer of material can advantageously be protected from solvents used to attach the first and second layer to the first surface of the prism and which might be harmful to the polymers and fluid in the first layer.

In another aspect of the present invention, the first surface of the light refractor can be covered with only a single layer of polymer, which can be stiff or rigid, but need not be. This layer of polymer can have a surface which is relatively smoother than the ground surface of the prism. As a result, relatively more complete contact between a fingerprint ridge and an imaging surface of the image capturing system can be realized. This can advantageously allow the image capturing system to generate a higher contrast, sharper fingerprint image.

DETAILED DESCRIPTION

Figure 3:
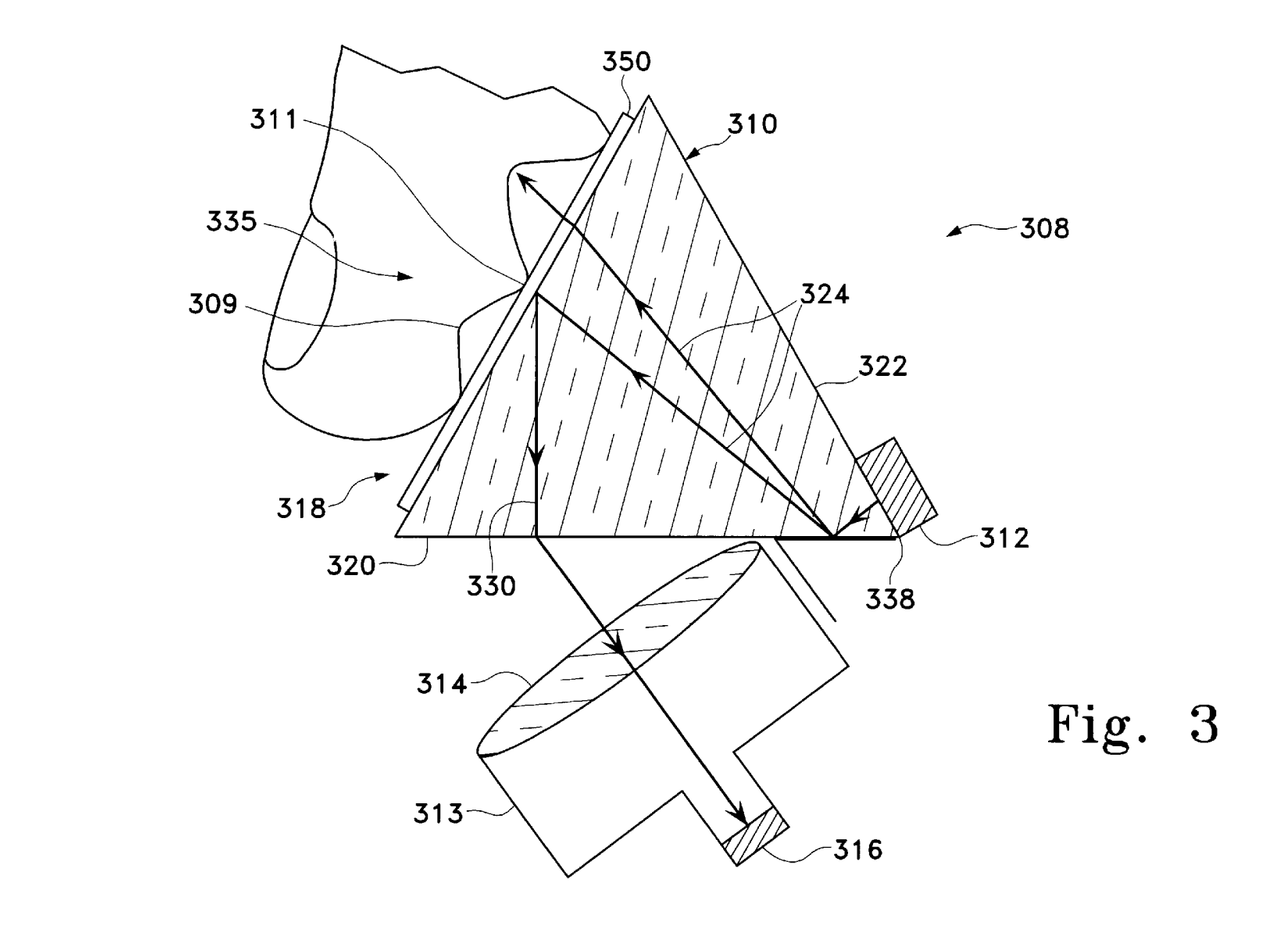
FIG. 3 is a schematic side view of a scattering image capturing system including an optical prism having a surface with a first layer of material applied thereto in accordance with the present invention.

FIG. 3 shows an image capturing system 308 in accordance with the present invention. System 308 includes light refractor for reflecting and refracting light, which is preferably a triangular prism 310; a light source 312; and a light receptor 313. Light detector 313 preferably includes a lens assembly 314 and an image sensor 316. Prism 310 is preferably a five faced isosceles triangular prism the length of which extends into the plane of FIG. 3. Prism 310 includes a rigid, rectangular light receiving surface 322 and rigid viewing surface 320 through which an image of a fingerprint 335 passes out of prism 310. In the embodiment of FIG. 3, prism 310 includes a rigid further surface between the light receiving surface 322 and viewing surface 320. The further surface forms part of imaging surface 318 which will be discussed in greater detail below. Light receiving surface 322 allows light to pass into prism 310 from light source 312 which faces light receiving surface 322. It is also within the scope of the present invention that light receiving surface 322 and viewing surface 320 be the same surface. Although the light refractor is preferably a prism 310, it is also considered that the light refractor be any other light refracting device, such as a concave, convex, or flat lens, which can provide a surface against which an object to be imaged can be placed.

Light source 312 is preferably an elongated LED array consisting of a single row of light emitting diodes (LEDs) extending the length (into the plane of FIG. 3) of prism 310. If such LEDs are used as light source 312, a diffusive cover can be placed between the LEDs and viewing surface 320 to provide more even illumination of imaging surface 318. It is also within the scope of the present invention, however, for light source 312 to be any other type of light source to provide incident light into prism 310. Preferably, light source 312 is placed along an edge 338 of prism 310 which is opposite imaging surface 318.

Light receptor 313 is for receiving scattered light 330 from fingerprint 335 and focusing scattered light 330 onto image sensor 316. Lens assembly 314 can be a single lens or, preferably, can consist of multiple lenses. Most preferably, lens assembly 314 has a focal length of approximately 13.48 mm and is located approximately 13.5 mm from viewing surface 320. Additionally, lens assembly most preferably consists of three lenses whose respective optical axes are aligned on a common optical axis. A first lens most preferably has a diameter of approximately 17.8 mm, and second and third lenses most preferably have a diameter of approximately 6 mm. It is considered that any number of lenses be included in lens assembly 314.

Image sensor 316 captures optical light images from lens assembly 314 and converts them to electrical signals. Image sensor 316 can be a charge coupled device ("CCD") or any other means of converting a light signal into either an analog or digital electrical signal. Preferably, image sensor 316 is a complementary metal oxide semiconductor device ("CMOS"). CCD and CMOS image sensors are well known by those skilled in the art. The electrical signals generated by image sensor 316 can be processed using known means and used to compare input patterns, such as fingerprints.

Figure 4:
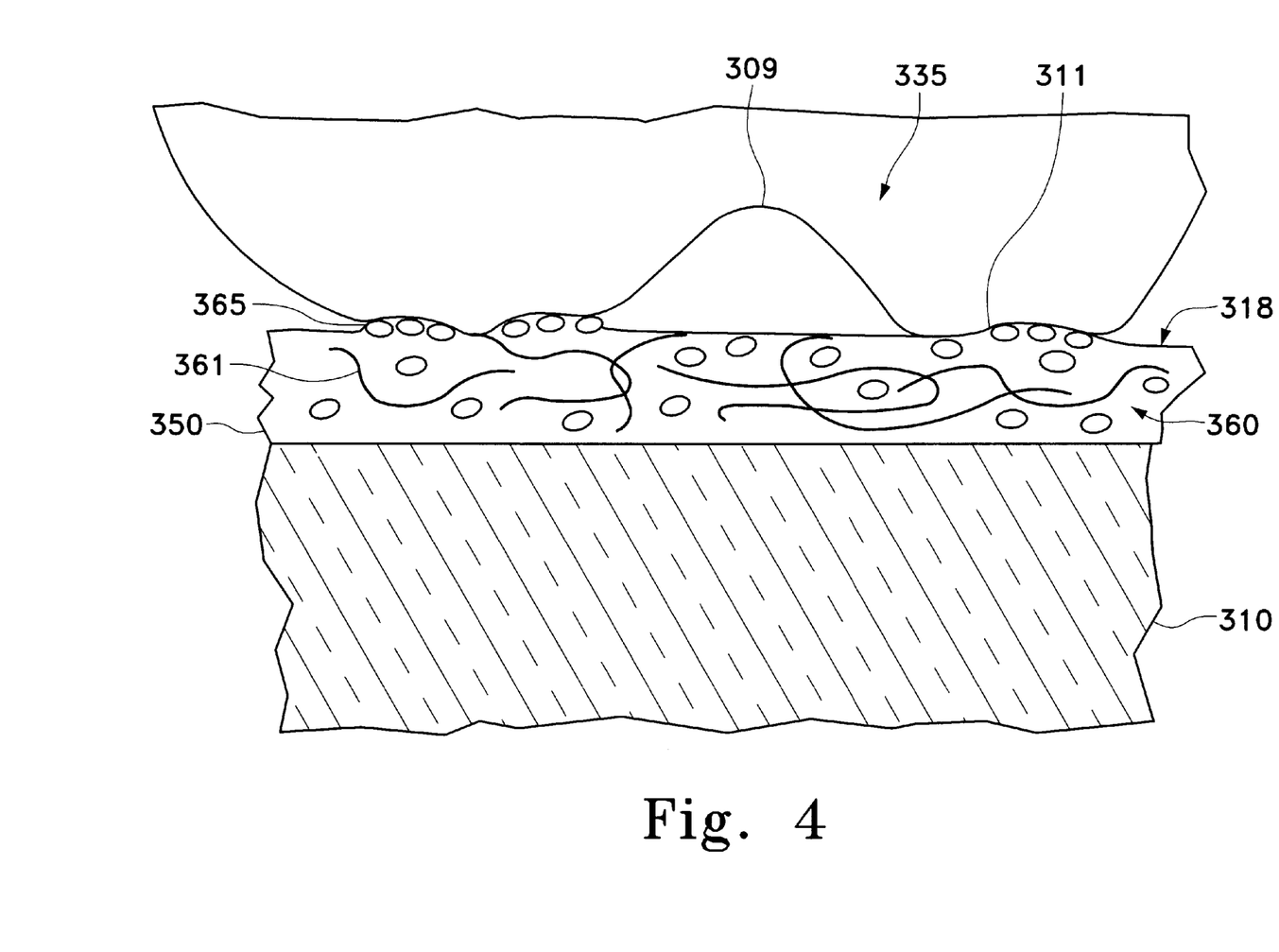
FIG. 4 is a partial side schematic view of the optical prism shown in FIG. 3 with a fingerprint placed on the imaging surface thereof.

As noted in the background section, if a fingerprint is placed directly against a rigid surface of prism 310, fingerprint ridges may not fully contact the rigid surface at locations of irregularities and indentations in the fingerprint ridges. This can result in an unclear or relatively low contrast fingerprint image. As such, imaging surface 318 includes at least a first layer 350 of material placed directly adjacent to prism 310. As shown in FIG. 4, which is a schematic side view of imaging surface 318, first layer 350 includes at least a first part formed of polymer 360. As FIG. 4 shows in highly enlarged schematic detail, a polymer 360 is formed of polymer chains 361 and, as discussed in detail below, can be used by itself. However, first layer 350 can also include a second part formed of a fluid 365 which can be relatively oily, but need not be. Polymer 360 can be stiff or hard, but need not be, and acts to retain the fluid 365 as part of first layer 350. The fluid 365 can be displaced from one site in layer 350 to another site therein. In this way, as shown in FIG. 4, when a fingerprint 335 is placed against imaging first layer 350, fluid 365 can be drawn to the surface of layer 350 to fill in irregularities in fingerprint ridges 311. However, because a fingerprint valley will typically be much larger than an irregularity in a fingerprint ridge, fluid 365 will not be drawn into a fingerprint valley 309.

Accordingly, to create an optical image of fingerprint 335 on image sensor 316, fingerprint 335 is placed against first layer 350 of imaging surface 318. Incident light 324 from light source 312 passes through light receiving surface 322 and into prism 310 to strike imaging surface 318. Though it need not be, in the embodiment shown, image capturing system 308 is a scattering system. As such, most incident light 324 will strike imaging surface 318 at an angle less than the critical angle of imaging surface 318. Accordingly, incident light 324 which strikes imaging surface 318 at a region thereof where there is a fingerprint valley 309 will substantially pass through imaging surface 318, including first layer 350, such that substantially no light hitting an area of imaging surface 318 where there is a fingerprint valley 309 will be directed through viewing surface 320. However, incident light 324 that strikes a region of imaging surface 318 where there is a fingerprint ridge 311 will substantially scatter off of fingerprint ridge 311, producing scattered light 330. A portion of scattered light 330 will exit prism 310 via viewing surface 320. Upon exiting prism 310, scattered light 330 will refract into light receptor 313 to create an image of fingerprint 335.

As noted above, the fluid 365 in layer 350 of imaging surface 318 acts to fill in irregularities in fingerprint ridges 311. This creates the same boundary condition between a fingerprint ridge 311 and the imaging surface 318 both at points where fingerprint ridge 311 has no irregularities 117 and at points where there are indentations or irregularities 117. As such, substantially the entire surface of a fingerprint ridge 311, whether at a point of an irregularity 117 or not, will cause incident light 324 to scatter to create an image of fingerprint 335. Because substantially the entire fingerprint ridge 311 scatters incident light 324 to create an image, regardless of whether incident light 324 strikes an irregularity or indentation in ridge 311, a relatively high contrast, sharp fingerprint image is advantageously produced by image capturing system 308.

Advantageously, such high contrast images can be produced without the need to use a separate pad to supply chemicals to a fingerprint as in Arndt, discussed in the background section. Moreover, it has been determined that the fluid 365 present in first layer 350 can tend to dissolve the oily substances which, as discussed in the background section, can be contained in a fingerprint. Accordingly, there is a reduced likelihood of oily residue being left on imaging surface 318 which could interfere with subsequent capturing of fingerprint images and collect debris, which could also interfere with capturing of fingerprint images. Further, there is a reduced likelihood that such oily residue could leave a fingerprint image which could "trick" image capturing system 308 to registering a false match.

Polymers that can be used for polymer 360 include, but are not limited to, polyvinyl chloride (PVC), low density polyethylene (LDPE), poly(ethylene terephthalate) (PET) and poly(ethylene naphthalate) (PEN) or any combination thereof. Preferably, polymer 360 is PVC. Fluid 365 is preferably a plasticizer. Plasticizers which can be used for fluid 365 can include, but are not limited to, dioctyl phthalate (DOP), di(2-ethylhexyl) phthalate (DEHP), and/or dibutyl phthalate. Preferably, up to 70% by weight of the first layer 350 of material can be composed of plasticizers. More preferably, from 30% to 60% of first layer 350 is composed of plasticizer.

Figure 8:
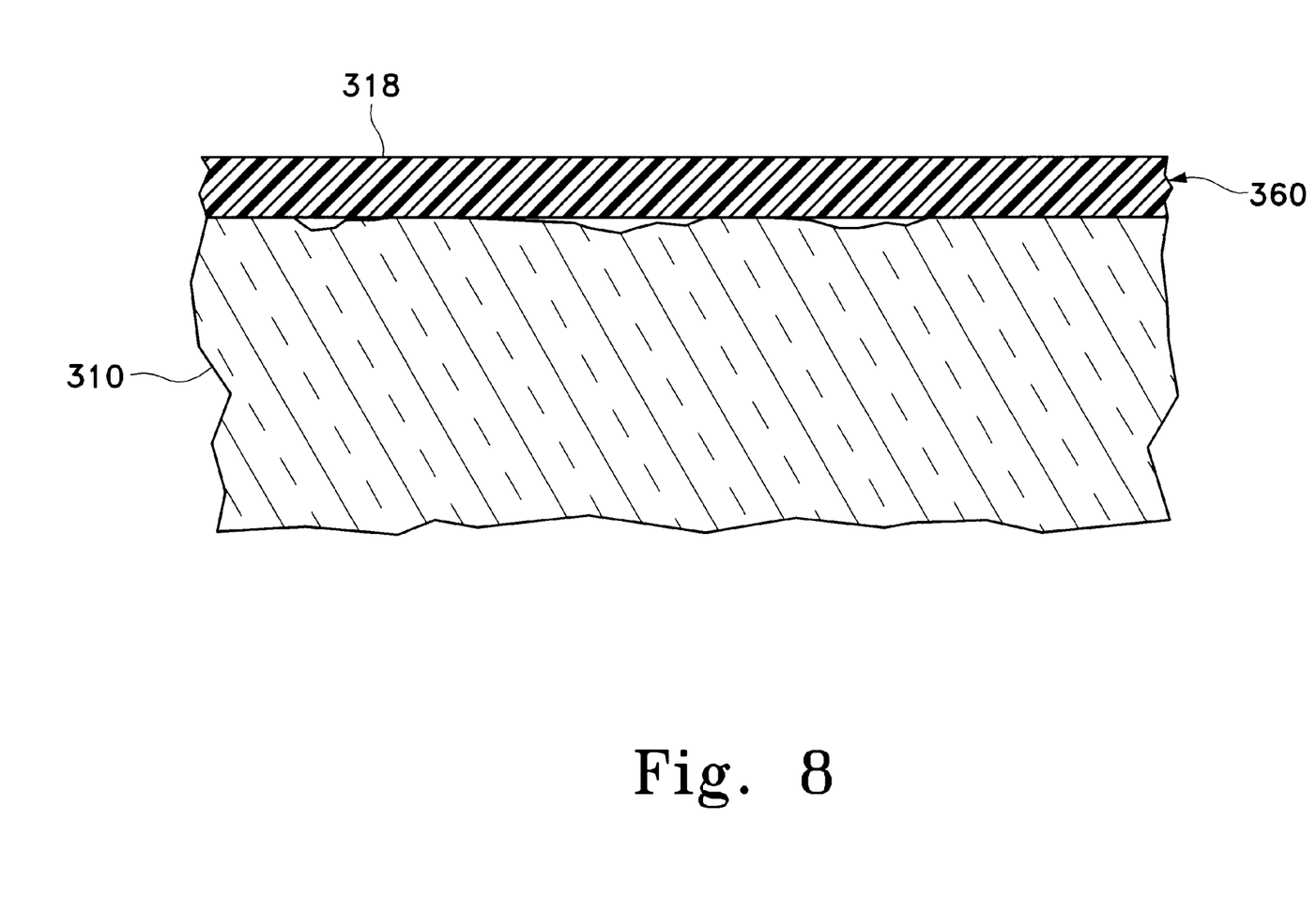
FIG. 8 is a partial side schematic view of the optical prism shown in FIG. 3 with a single layer of polymer coating on one face thereof.

Preferably, polymer 360 is formed by casting, which is a processes that is well known to those skilled in the art. By casting polymer 360, the surface formed can be relatively smoother than ground glass surface of a prism would be. Accordingly, as shown in FIG. 8, it is also within the scope of the present invention to form first layer 350 entirely from a polymer which can be hard and non-pliable, though it need not be. Such polymers can include, but are not limited to, polyesters such as hard coated poly(ethylene terephthalate) (PET) and poly(ethylene naphthalate) (PEN); polyurethane (PU); polyolefins such as polyethylene (PE) and polypropylene (PP) composed of random polymers or syndiotactic PP; epoxy; and heat-curable acrylic polymers such as melamine containing polyacrylic mixtures. In this way, the occurrence and size of pits, such as pits 119 shown in FIG. 2, on imaging surface 318 can be reduced. Thus, relatively more complete contact between imaging surface 318 and fingerprint ridges 311 can be realized. This can advantageously improve the contrast and sharpness of an image captured by image capturing system 308.

Figure 5:
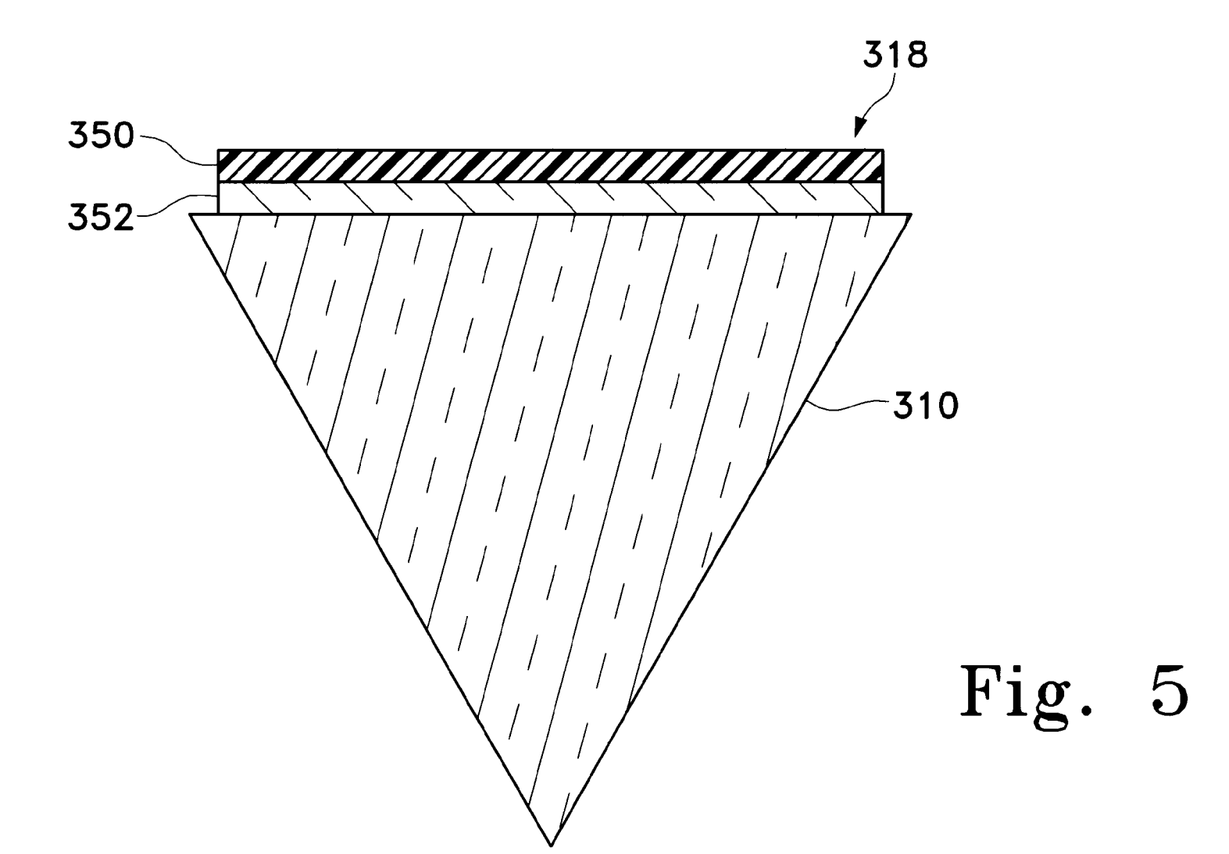
FIG. 5 is a side view of the optical prism shown in FIG. 3 including a second layer of material interposed between the first layer of material and a surface of the optical prism.

Some materials which can be used in first layer 350 can be broken down by solvents in adhesives used to adhere the first layer 350 to prism 310. Such materials include PVC and some plasticizers. Adhesives that can be harmful to these materials can include polyacrylic adhesives which can include solvents such as acetone, toluene and alcohol. As such, as shown in FIG. 5, which is a side view of prism 310 and imaging surface 318, a second layer 352 of transparent material can be placed between the first layer 350 and the surface of prism 310 to prevent contact between first layer 350 and an adhesive used on the surface of prism 310. This second layer 352 is preferably resistant to break-down or deterioration by adhesives which may be used to adhere the second layer 352 to the surface of prism 310. Transparent materials which can be used to form layer 352 can include, for example: polyesters such as poly(ethylene terephthalate) (PET) and poly(ethylene naphthalate) (PEN); polyurethane (PU); polyolefins such as polyethylene (PE) and polypropylene (PP) composed of and random polymers or syndiotactic PP. These materials are generally resistant to deterioration or break-down by solvents which might be contained in acrylic adhesives.

To avoid contact between first layer 350 and acrylic adhesives containing solvents which may be harmful to first layer 350, first layer 350 is preferably adhered to second layer 352 by a heat bond or any other type of bond which avoids use of an adhesive containing solvents. As discussed below, sheets of PVC having a layer of PET adhered thereto by a heat bond are available commercially. Such a bond would be difficult to realize between the surface of prism 310 and a layer of PVC placed directly on the surface of prism 310 because the hard surface of prism 310 is relatively un-susceptible to such a bond. However, any of the polyesters, polyolefins, or other materials mentioned above for use as part of layer 352 are susceptible to such a bond with the first layer 350 of polymer. By interposing deterioration resistant second layer 352 between first layer 350 and the surface of prism 310, first layer 350, can advantageously be used without being deteriorated by adhesives used on the surface of prism 310. It is also considered to bond first layer 350 to second layer 352 using an adhesive which is not harmful to the first layer 350. Also, if second layer 352 is not used, the first layer 350 can be adhered to the prism surface using an adhesive which is not harmful to first layer 350.

Preferably, if both first layer 350 and second layer 352 are used, the combination of both second layer 352 and first layer 350 is from 0.1 to 1 mm thick and more preferably from 0.3 to 0.5 mm thick. Additionally, the ratio of thickness of first layer 350 to second layer 352 can be any value but is preferably approximately 1:3. If just first layer 350 is used, first layer 350 is preferably from 0.1 to 1 mm thick.

Hard coated PET can be obtained from SKC Co., Ltd. of Suwon Kyunggi-do, Korea. PVC and PU can be obtained from UreTech, Ltd. of Ansan Kyunggi-do, Korea. Sheets of PVC containing plasticizers and having a layer of PET heat bonded thereto, with adhesive already applied to the PET, can be obtained from Hanyangsanup Ltd. Kwangju Kyunggi-do, Korea. Sheets of PVC with solvent-free adhesive are also available from Hanyangsanup Ltd. Curable hard epoxy is commercially available under the trade name "EnviroTex Lite pour-on" from Environmental Technology, Inc. of Fields Landing, Calif.

Figure 6:
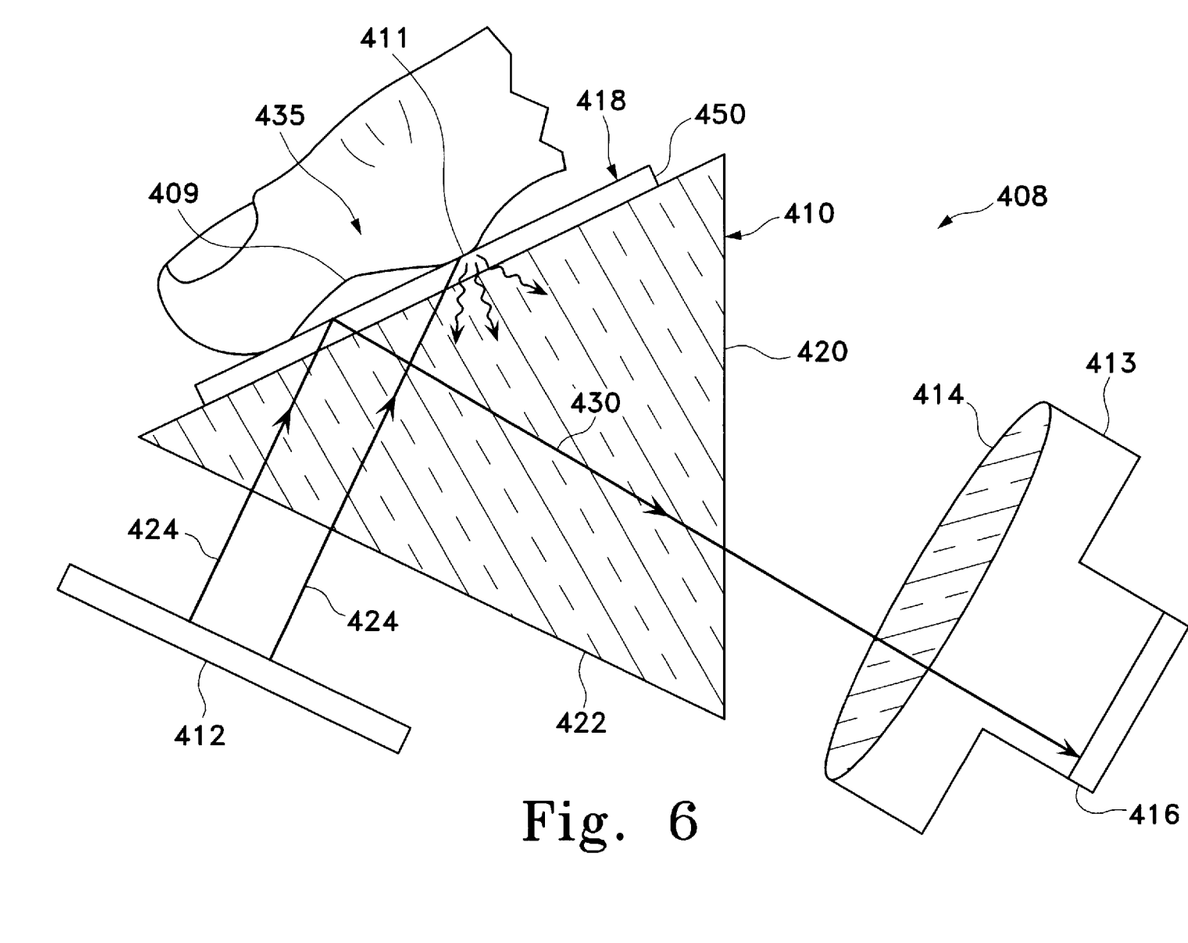
FIG. 6 is a schematic of an absorption image capturing system including an optical prism having a surface with a first layer of material applied thereto in accordance with the present invention.

Although image capturing system 308 is a scattering type system, it is also contemplated that a layer of polymer containing fluid, with or without a protective layer, be included in an imaging surface of other types of image capturing systems such as absorption type systems, discussed in the background section, or any other type of image capturing system. Such an absorption type image capturing system 408 is shown in FIG. 6. Like image capturing system 308, image capturing system 408 includes a light refractor in the form of a triangular prism 410; a light source 412; and a light receptor 413. Prism 410 includes a light receiving surface 422 and a viewing surface 420. An imaging surface 418 of system 408 includes a rectangular face of prism 410 between viewing surface 420 and imaging surface 418 and at least a first layer 450 of material. First layer 450 is substantially the same as first layer 350 described above. Light source 412 can be substantially the same as light source 312 and is adjacent to light receiving surface 422.

Light receptor 413 is substantially the same as light receptor 313 and includes lens assembly 414 and light detector 416.

To image a fingerprint 435 placed against imaging surface 418, light source 412 provides incident light 424 which enters light receiving surface 422 to strike imaging surface 418. Light source 412 is positioned such that incident light 424 will strike imaging surface 418 at an incident angle greater than the critical angle of imaging surface 418. Accordingly, incident light which strikes regions of imaging surface 418 where there is a fingerprint valley 409 will totally internally reflect off of imaging surface 418. Totally internally reflected light 430 will then enter light receptor 413. However, incident light 424 which strikes an region of imaging surface 418 where there is a fingerprint ridge 411 touching imaging surface 418 will scatter from and be absorbed by fingerprint ridge 411. Accordingly, relatively less light from a fingerprint ridge 411 will enter light receptor 413. In this way, an image of fingerprint 435 in which fingerprint valleys 409 are relatively bright and fingerprint ridges 411 are relatively dark is received by image receptor 413.

Figure 7:
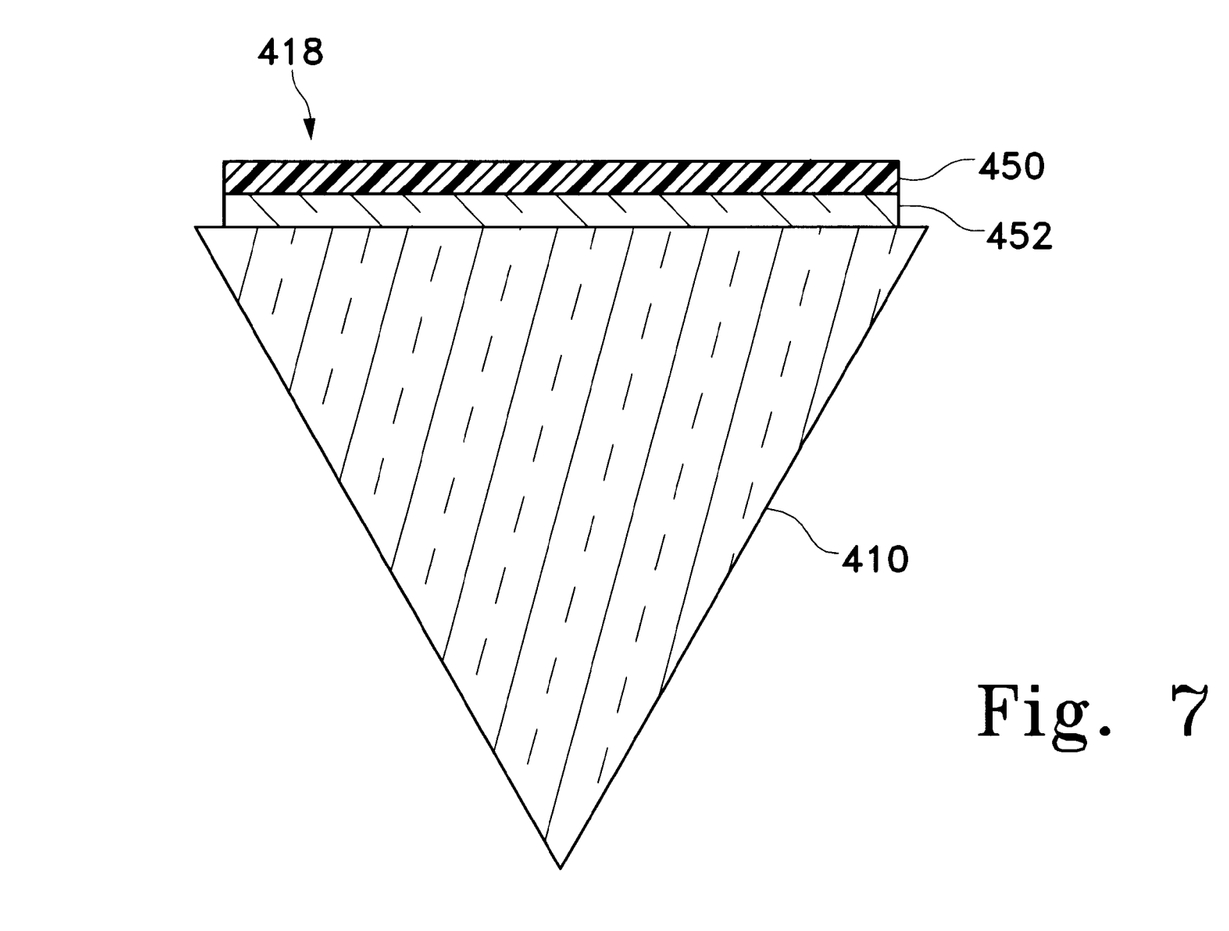
FIG. 7 is a side view of the optical prism shown in FIG. 6 including a second layer of material interposed between the first layer of material and a surface of the optical prism.

First layer 450 of imaging surface 418 acts in substantially the same way, and can be formed from the same materials, as first layer 350 of imaging surface 318, described above, to enhance the contrast, accuracy, and clarity of a fingerprint 435 image captured by image capturing system 408. Additionally, as shown in FIG. 7, a second layer 452 of material can be interposed between first layer 450 and the surface of prism 410. This second layer 452 acts in substantially the same manner, and can be formed from the same materials, as second layer 352 to protect first layer 450 from deterioration due to exposure to solvents in adhesives used on the surface of prism 410.

Many widely different embodiments of the present invention may be constructed without departing from the spirit and scope of the present invention. It should be understood that the present invention is not limited to the specific embodiments described in the specification.

What is claimed is:

1. An apparatus for capturing the image of a patterned object comprising:
    a transparent light refractor for reflecting and refracting light, the light refractor including at least a first surface, wherein a patterned object may be placed adjacent to the first surface;
    a light source adjacent to the light refractor, wherein the light source transmits incident light into the transparent light refractor towards the first surface of the light refractor to generate an image of the patterned object;
    a light receptor adjacent to the light refractor for capturing an image of the patterned object placed adjacent to the first surface, wherein at least a portion of the incident light transmitted into the light refractor toward the first surface of the light refractor may be reflected off of the first surface and received by the light receptor;
    a first layer of material disposed on the first surface of the light refractor, the first layer of material being substantially transparent and having at least two parts, a first part comprising a polymer and a second part comprising a fluid retained by the polymer, such that the fluid is adapted to fill irregularities in surfaces of a patterned object substantially in contact with the first layer of material; and
    a second layer of substantially transparent material interposed between the first layer of material and the first surface of the light refractor.

2. The apparatus of claim 1 wherein the light refractor comprises a triangular prism having three rectangular faces, wherein the first surface is disposed on a rectangular face of the triangular prism, and the light receptor and the light source are each positioned adjacent to a rectangular face of the triangular prism.

3. The apparatus of claim 2 wherein the polymer of the first layer of material comprises polyvinyl chloride and the fluid of the first layer of material comprises at least one plasticizers.

4. The apparatus of claim 3 wherein the at least one plasticizer is selected from the group consisting of dioctyl phtalate (DOP), di(2-ethylhexyl) phtalate (DEHP), and dibutyl phtalate.

5. An apparatus for capturing an image of a patterned object comprising:
    a transparent light refractor for reflecting and refracting light, the light refractor including at least a first surface, wherein the patterned object to be imaged may be placed adjacent to the first surface;
    a light source adjacent to the light refractor, wherein the light source transmits incident light into the transparent light refractor towards the first surface of the light refractor to generate an image of the patterned object;
    a light receptor adjacent to the light refractor for receiving an image of the patterned object to be placed against the first surface, wherein at least a portion of the incident light transmitted through the refractor by the light source may be reflected off of the first surface and received by the light receptor;
    a first layer of material provided on the first surface of the light refractor, the first layer of material being transparent and having at least two parts, a first part comprising a polymer and a second part comprising a fluid retained by the polymer, wherein the fluid is adapted to fill irregularities in surfaces of the patterned object that are substantially in contact with the first layer of material; and
    a second layer of transparent material interposed between the first layer of material and the first surface of the light refractor.

6. The apparatus of claim 5 wherein:
    the second layer is adhered to the first surface of the light refractor, wherein the second layer of material is resistant to deterioration by the acrylic adhesive; and
    the first layer is adhered to the second layer of material using a heat bond and the first layer does not come into contact with the acrylic adhesive.

7. The apparatus of claim 6 wherein the second layer of material is selected from the group consisting of polyurethane, polyethylene, poly(ethylene terephthalate), hard coated poly(ethylene terephthalate), poly(ethylene naphthalate), polypropylene, and curable epoxy.

8. The apparatus of claim 7 wherein the patterned object to be imaged is a fingerprint.

9. An apparatus for capturing the image of a patterned object comprising:
    a transparent light refractor for reflecting and refracting light, the light refractor including at least a first surface, wherein a patterned object to be imaged may be placed adjacent to the first surface;
    a light detector adjacent to a second surface of the light refractor for detecting an image of the patterned object to be placed against the first surface;
    a light source adjacent to a third surface of the light refractor which directs light towards the first surface of the light refractor to generate an image of the patterned object;

a first layer of material provided on the first surface of the light refractor, the first layer of material comprising a polymer formed by casting; and a second layer of substantially transparent material interposed between the first layer of material and the first surface of the light refractor.

10. The apparatus of claim 9 wherein the first layer of material is selected from the group consisting of poly(ethylene terephthalate), hard coated poly(ethylene terephthalate), poly(ethylene naphthalate), polyurethane, polyethylene, polypropylene, curable epoxy, and melamine containing polyacrylic mixtures.

11. The apparatus of claim 9, wherein the first layer comprises a polymer that is substantially transparent and substantially non-pliable.

12. A system for creating an image of a patterned object comprising:

a transparent light refractor for reflecting and refracting light, the light refractor including at least a first surface, wherein a patterned object to be imaged may be placed adjacent to the first surface;

a light source adjacent to the light refractor, wherein the light source transmits incident light into the transparent light refractor towards the first surface of the light refractor to generate an image of the patterned object;

a light receptor adjacent to the light refractor for receiving an image of the patterned object to be placed against the first surface, wherein at least a portion of the incident light transmitted through the refractor by the light source may be reflected off of the first surface and received by the light receptor;

a first layer disposed on the first surface of the light refractor, the first layer comprising a polymer and a fluid retained by the polymer, wherein the fluid is adapted to fill irregularities in the surfaces of the patterned object that are substantially in contact with the first layer of material; and a second layer interposed between the first layer of material and the first surface of the light refractor.

13. An apparatus for capturing the image of a patterned object comprising:

a transparent light refractor for reflecting and refracting light, the light refractor including at least a first surface adjacent to which a patterned object to be imaged is to be placed;

a light source adjacent to the light refractor that directs light toward the first surface to generate an image of the patterned object, wherein the light source transmits incident light into the transparent light refractor towards the first surface of the light refractor;

a light detector adjacent to the light refractor for detecting an image of the patterned object to be placed against the first surface, wherein at least a portion of the incident light transmitted into the light refractor toward the first surface of the light refractor may be reflected off of the first surface and received by the light detector;

a first layer of material provided on the first surface of the light refractor, the first layer of material being transparent and having at least two parts, a first part which is a polymer and a second part which is a fluid and which is retained by the polymer, such that the fluid can fill irregularities and gaps in a patterned object to be imaged which is placed on the first layer of material; and a second layer of transparent material interposed between the first layer of material and the first surface of the light refractor.

14. The apparatus of claim 13 wherein:

the second layer of material is adhered to the surface of the light refractor by acrylic adhesive to which the second layer of material is resistant to deterioration; and the first layer of material is adhered to the second layer of material using a heat bond, such that the first layer of material does not come into contact with the acrylic adhesive.

15. The apparatus of claim 14 wherein the second layer of material is selected from the group consisting of polyurethane, polyethylene, poly(ethylene terephthalate), hard coated poly(ethylene terepthalate), poly(ethylene napthalate), polypropylene, and curable epoxy.

16. The apparatus of claim 15 wherein the patterned object to be imaged is a fingerprint.

* * * * *